United States Patent [19]
Koppel et al.

[11] Patent Number: 5,272,253
[45] Date of Patent: Dec. 21, 1993

[54] CLUSTER CONJUGATES OF DRUGS WITH ANTIBODIES

[75] Inventors: Gary A. Koppel, Indianapolis, Ind.; Robin E. Offord, Collex-Bossy; Keith Rose, Geneva, both of Switzerland; William L. Scott, Indianapolis, Ind.

[73] Assignee: Eli Lilly and Company, Indianapolis, Ind.

[21] Appl. No.: 724,030

[22] Filed: Jul. 1, 1991

[51] Int. Cl.$^5$ ............................................... C07K 7/02
[52] U.S. Cl. .................................. 530/332; 530/326; 530/327; 530/328; 530/329; 530/345; 530/391.1
[58] Field of Search ............................ 424/85.8, 85.91; 530/387, 389, 391, 326, 329, 332, 345, 391.1

[56] References Cited

U.S. PATENT DOCUMENTS

| | | | |
|---|---|---|---|
| 4,046,722 | 9/1977 | Rowland | 260/424 |
| 4,543,211 | 9/1985 | Kato et al. | 260/112 B |
| 4,587,046 | 5/1986 | Goodman et al. | 530/330 |
| 4,867,973 | 9/1989 | Goers et al. | 424/85.91 |
| 5,006,652 | 4/1991 | Cullinan et al. | 540/478 |

FOREIGN PATENT DOCUMENTS

| | | |
|---|---|---|
| 243929 | 11/1987 | European Pat. Off. |
| 359428 | 3/1990 | European Pat. Off. |
| 360433 | 3/1990 | European Pat. Off. |

OTHER PUBLICATIONS

Tam, "High-Density Multiple Antigen-Peptide System for Preparation of Antipeptide Antibodies", *Methods in Enzymology*, vol. 168, pp. 7-15 (1989).
Umemoto et al., "Preparation and In Vitro Cytotoxicity of Methotrexate-Anti-MM46 Monoclonal Antibody Conjugate Via An Oligopeptide Spacer", *Int. J. Cancer.* 43, 677-684 (1989).
Kato et al., "A Novel Method of Conjugation of Daunomycin with Antibody with a Poly-L-glutamic Acid Derivative as Intermediate Drug Carrier. An Anti--α-fetoprotein Antibody-Daunomycin Conjugate", *J. Med. Chem.* 27, 1602-1607 (1984).
Hurwitz et al., "A Conjugate of 5--Fluorouridine-Poly(L-lysine) and an Antibody Reactive with Human Colon Carcinoma", *Bioconjugate Chem.*, vol. 1, No. 4, 285-90 (1990).
Offord and Rose, "Press-Stud Protein Conjugates", Protides of the Biological Fluids, 35-38 (1986).
Rose et al., Peptides 1988, 274-76.
Pochon et al., "A Novel Derivative of the Chelon Desferrioxamine for Site-Specific Conjugation to Antibodies", *Int. J. Cancer.* 43, 1188-1194 (1989).
Abstract No. 117, Vilaseca et al., San Diego Immunoconjugates for Cancer Meeting, Mar. 15-17, 1990.
Jones et al., Poster Session, San Diego Immunoconjugates for Cancer Meeting, Mar. 15-17, 1990.
Fisch et al., Poster Session, San Diego Immunoconjugates for Cancer Meeting, Mar. 15-17, 1990.
Jones et al., Poster Session and Abstract, St. Gall, Switzerland, Feb. 28, 1990.

*Primary Examiner*—Robert J. Hill, Jr.
*Assistant Examiner*—Sally Teng
*Attorney, Agent, or Firm*—John E. Parrish; Robert A. Conrad; Leroy Whitaker

[57] ABSTRACT

Targeted drug conjugates which enable a large number of molecules of drug to be directed to a cell by a single molecule of antibody are provided. The invention also provides intermediates for the synthesis of such conjugates and cytotoxic drugs modified in accordance with the cluster concept of the invention.

9 Claims, No Drawings

CLUSTER CONJUGATES OF DRUGS WITH ANTIBODIES

FIELD OF THE INVENTION

The present invention belongs to the fields of organic chemistry, pharmaceutical chemistry and immunology, and provides vehicles for targeting large doses of cytotoxic drugs to undesirable cells. Antibodies, preferably monoclonal antibodies, are the targeting agents, and linker chemistry is provided which allows each antibody to carry multiple molecules of drug. Intermediates for the preparation of the conjugates are also provided.

BACKGROUND OF THE INVENTION

Pharmaceutical chemists have worked over the years to provide more specific and potent drugs for the treatment of disease. In the case of cancer and other diseases which function by the creation of specific abnormalities of cells, most of the useful drugs have been of the cytotoxic type, which function by killing the abnormal cell. Such drugs are, of course, quite potent, and hazardous, even life-threatening, side effects are not uncommon. Thus, efforts have been made for some time to develop a mechanism for targeting such drugs directly to the cell to be affected, without administering a whole-body dose of the cytotoxic drug. Many patents and articles have been published on efforts to use antibodies for the targeting of such drugs. However, up to the present time, no antibody-drug conjugate has been approved for therapeutic use.

The present invention carries the science of drug targeting an additional major step forward, by providing controllable linker chemistry which allows the convenient attachment of multiple molecules of cytotoxic drug to a single molecule of antibody.

SUMMARY OF THE INVENTION

The present invention provides a physiologically-acceptable drug conjugate of the formula

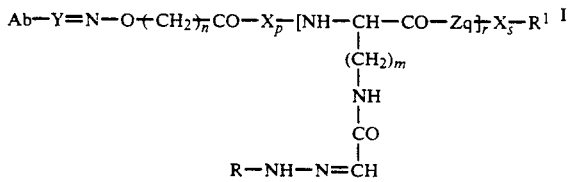

wherein
Ab is an antibody or antigen-recognizing fragment thereof which recognizes an antigen associated with an undesirable cell;
R is the residue of a drug having a cytotoxic effect on the cell;
$R^1$ is a hydroxy group or a carboxy-protecting group;
X is $—NH—(CH_2)_t—CO—$;
Z is

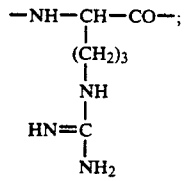

(A)

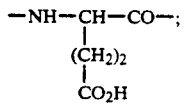

(B)

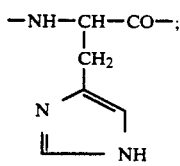

(C)

or

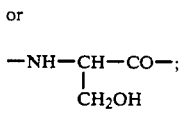

(D)

m is from 2 to about 6;
n is from 1 to about 4;
p is from 0 to about 5;
q is from 0 to about 3;
r is from 1 to about 10;
s is 0–2;
t is from 1 to about 3, and the values of t in the various X groups are independent of each other;
Y is a bond or a linking group of the formula
(E) $—NH—NH—CO—NH—N=CH—R^2—HC=$ or
(F) $—CO—R^4—R^3—R^2—HC=$;
$R^2$ is $C_1$–$C_5$ alkylene, phenylene or pyrrolyl;
$R^3$ is a bond or $—NH—CO—$;
$R^4$ is a bond or $C_1$–$C_5$ alkylene;
provided that neither $R^3$ nor $R^4$ is a bond unless both $R^3$ and $R^4$ are bonds;
wherein each molecule of Ab is bonded to from 1 to about 10 $—Y=$ linkages.

the invention also provides pharmaceutical compositions comprising a conjugate of the invention and a parenterally-administerable medium, and treatment methods comprising the parenteral administration of a conjugate of the invention to a patient in need of treatment with the drug.

The invention also provides intermediates for preparing the conjugates, which intermediates are of the formulae

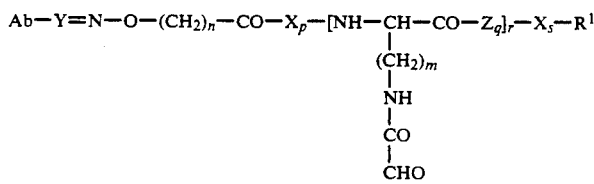

-continued

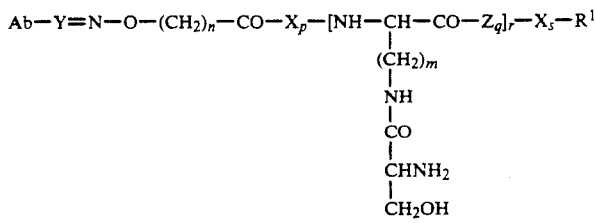

III

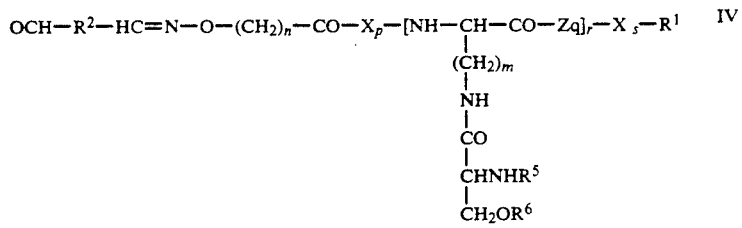

IV

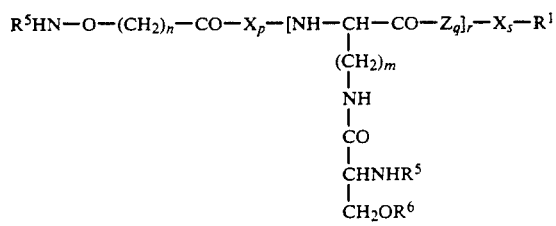

V the $R^5$ groups independently represent the same or different amino-protecting groups or hydrogen;
$R^6$ is a hydroxy-protecting group or hydrogen;

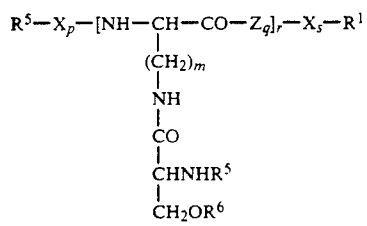

VI

Further, the invention provides a modified drug of the formula

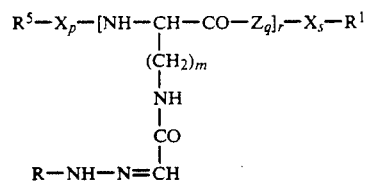

VIII

DETAILED DESCRIPTION OF THE INVENTION

Throughout the present document, all temperatures are in degrees Celsius. All expressions of percentage, concentration and the like are in weight units, unless otherwise stated. All references to concentrations and dosages of drug conjugates are in terms of the amount or concentration of the drug contained in the conjugate.

In the above formulae, the general and specific chemical terms used have their normal meanings in organic, and especially amino acid, chemistry. For example, the term $C_1$–$C_5$ alkylene refers to groups such as methylene, ethylene, propylene and isoprpylene, n-butylene and isobutylene, 1,3-dimethylpropylene and the like. The term phenylene refers to a phenyl group linked at the meta or para positions, and a pyrrolyl group may be linked at any positions but preferably at the 2,5-positions.

The groups Y, $R^3$ and $R^4$ may represent bonds. When Y is indicated as being a bond, the meaning is that the antibody or antibody fragment is attached by a double bond directly to the nitrogen adjacent the group Y. When $R^3$ and $R^4$ are bonds, the group $R^2$ is joined directly to the carbonyl which terminates the Y group.

It will be understood that the linker compounds and intermediates are often made up of chains and assemblies of amino acids. The formulae above do not identify the stereochemical form of such amino acids, and the present invention contemplates that any configuration, natural or unnatural, is functional.

It is preferred to use an amino acid of a single form, not a mixture, at any given position.

The term, hydroxy-protecting group, in the formulae above refers to any of the groups which are used by organic chemists to protect hydroxy groups while reactions are carried out on other functional portions of a molecule, and are well discussed in conventional text books, especially Chapter 2 of Greene, Protective Groups in Organic Synthesis, John Wiley and Sons, New York (1981). Typical such hydroxy-protecting groups include formyl, 2-chloroacetyl, benzyl, diphenylmethyl, triphenylmethyl, 4-nitrobenzoyl, phenoxycarbonyl, t-butyl, methoxymethyl, tetrahydropyranyl, allyl, tetrahydrothienyl, 2-methoxy-ethoxymethyl, methoxyacetyl, phenoxyacetyl, isobutyryl, t-butoxycarbonyl, ethoxycarbonyl, benzyloxycarbonyl, and the like.

Amino-protecting groups are discussed in Chapter 7 of the Greene textbook mentioned above, and particularly include such groups as methoxycarbonyl, diisopropylmethyl, methoxycarbonyl and the like, 9-fluorenylmethoxycarbonyl (Fmoc) (which is particularly preferred), ethoxycarbonyl and haloethoxycarbonyl, formyl, acetyl and haloacetyl, alkanoates such as propionyl, arylpropionyl and the like, butyryl and halobutyryl, benzoyl and substituted benzoyl such as 4-methoxybenzoyl, and other groups which are commonly known and used by synthetic organic chemists.

Carboxy-protecting groups are discussed at length in Chapter 5 of Greene. Such groups include, for example, esters and amides, especially esters. Alkyl esters such as methyl, methoxyethoxymethyl, trichloroethyl, methylthioethyl, methoxymethyl, and benzyloxymethyl are commonly used. Benzyl esters including diphenylmethyl and triphenylmethyl, 4-nitrobenzyl and 4-methoxybenzyl, and 4-halobenzyl are also useful. Triethylstannyl and tributylstannyl are also good protecting groups, as are alkenes such as allyl and cinnamyl esters, and cycloalkyls such as cyclopentyl and cyclohexyl esters, and the like. Greene explains the reactions used to place and remove these and numerous other carboxy-protecting groups.

A number of aspects of the present invention are preferred embodiments, and should be specifically mentioned. For example, each of the cytotoxic conjugate of formula I, the modified drug of formula VIII, and the various intermediates of formulae II-VI is a preferred embodiment of the invention. More particularly, the following brief paragraphs list individual aspects of the invention, each of which is a preferred embodiment. It will be understood that the limitations expressed as follows may be combined to define further, more limited preferred embodiments.

Ab recognizes an antigen associated with a cancer cell;
Ab is an antibody fragment;
R has a cytotoxic effect on a cancer cell;
R is of formula IX;
R is of formula X;
$R^1$ is hydroxy;
$R^1$ is a carboxy protecting group;
Y is a bond;
Y is group E;
Y is group F;
$R^2$ is phenylene or pyrrolyl;
$R^2$ is pyrrolyl;
$R^3$ and $R^4$ are bonds;
$R^3$ is —NH—CO—;
$R^4$ is $C_1$-$C_3$ alkylene;
each molecule of Ab is bonded to one —Y=linkage;
each molecule of Ab is bonded to from 1 to about five —Y=linkages;
each molecule of Ab is bonded to from about 3 to about eight —Y=linkages.

It will be understood that the above preferred terms and groups equally constitute preferred limitations on the cytotoxic conjugates, on the various intermediate compounds of formulae II-VI, and on the drug of formula VIII. A preferred intermediate is used to prepare a preferred conjugate or drug.

It is believed that the above structural formulae and discussion of preferred embodiments of the invention fully describe the conjugates, intermediates and modified drug which constitute the present invention. However, the chemistry of the present invention is somewhat complex and the nomenclature of the compounds is quite difficult. In order to assist the reader to comprehend all aspects of the present invention, a number of specific embodiments of the invention will be described in outline form. Since the nomenclature is so lengthy and difficult, the specific embodiments of the invention will be identified in tabular form by the identities of their individual components, using the coded designations in the structural formulae I through VIII. For example, the identity of the group Z is indicated by A, B, C, or D, in reference to the corresponding structures in formula I.

In the first table below, a group of intermediate compounds of formula VI is presented.

TABLE I

| p | t | z | q | r | t | s | m | $R^6$ | $R^1$ | $R^5(X_p)$ | $R^5(CHNHR^5)$ |
|---|---|---|---|---|---|---|---|---|---|---|---|
| 5 | 3 | D | 2 | 1 | 1 | 2 | 4 | Benzyl | OH | t-Boc | t-Boc |
| 3 | 2 | B | 3 | 3 | 3 | 2 | 6 | $CH_2OCH_3$ | OH | H | $CO_2CH_3$ |
| 2 | 3 | — | 0 | 9 | 1 | 1 | 3 | H | OH | $CO_2CCl_3$ | H |
| 4 | 1 | A | 1 | 10 | — | 0 | 5 | Acetyl | $OCH_2OCH_3$ | H | H |
| 0 | — | C | 1 | 5 | — | 0 | 2 | H | $OCH_2CCl_3$ | $CO_2CH_2CH_2SO_2CH_3$ | Fmoc |
| 1 | 3 | — | 0 | 7 | 2 | 1 | 4 | Allyl | $OC(CH_3)_3$ | $CO_2CH(CH_3)C_2H_5$ | H |
| 0 | — | D | 1 | 10 | 1 | 1 | 6 | $CH_2OC(CH_3)_3$ | OH | $CO_2Allyl$ | Acetyl |
| 5 | 1 | A | 3 | 4 | — | 0 | 2 | $CH_2CCl_3$ | OAllyl | H | H |
| 0 | — | — | 0 | 6 | 3 | 2 | 3 | H | OTrityl | H | Benzoyl |
| 1 | 1 | C | 2 | 1 | 2 | 1 | 5 | $CO_2CH_3$ | $OCH_2$(4-Br phenyl) | H | $COCH_2COCH_3$ |
| 2 | 3 | B | 0 | 8 | 1 | 1 | 4 | $CH_2$(4-Br phenyl) | OH | $CO_2CH_2$(4-$NO_2$ phenyl) | $COCH_2COCH_3$ |
| 4 | 2 | — | 0 | 2 | — | 0 | 6 | H | $OCH_2$(4-$NO_2$ phenyl) | Fmoc | $CO_2CH_2CH_2I$ | t is 1;
t is 2 or 3;
m is about 4;
m is from 2 to about 4;
m is from about 4 to about 6;
n is 1;
n is 1-2;
p is from 0 to about 3;
p is from about 3 to about 5;
p is about 3;
q is 0 or 1;
r is from about 3 to about 7;
r is from 1 to about 5;
r is from about 5 to about 10;
s is 0;
s is 1 or 2;

As will be explained below, the intermediate compounds of formula VI are used to prepare the intermediates of formula V. The following Table II presents a group of formula V compounds. In this table, the protecting groups $R^5$, $R^6$ and $R^1$, have been ignored, and the reader is to understand that the intermediates may be protected at those positions with conventional protecting groups, if it is convenient in the circumstances to do so.

TABLE II

| n | p | t | z | q | r | t | s | m |
|---|---|---|---|---|---|---|---|---|
| | | ($X_p$) | | | | ($X_s$) | | |
| 1 | 1 | 3 | — | 0 | 1 | — | 0 | 6 |
| 4 | 0 | — | — | 0 | 2 | 3 | 1 | 5 |
| 1 | 3 | 1 | D | 2 | 10 | — | 0 | 2 |

TABLE II-continued

| n | p | t | Z | q | r | t | s | m |
|---|---|---|---|---|---|---|---|---|
| 3 | 5 | 2 | A | 1 | 4 | 1 | 2 | 3 |
| 1 | 0 | — | B | 3 | 6 | 2 | 1 | 2 |
| 1 | 2 | 1 | — | 0 | 8 | 1 | 1 | 6 |
| 2 | 1 | 3 | C | 1 | 2 | — | 0 | 5 |
| 4 | 5 | 1 | D | 3 | 7 | — | 0 | 4 |
| 1 | 4 | 2 | — | 0 | 3 | 1 | 2 | 3 |

The intermediates of formula IV, which are prepared by an additional step from the intermediates of formula V, are exemplified by compounds such as those which have been described in Tables I and II, modified by the addition of the bis-aldehyde group. The $R^2$ component of that group is further exemplified by groups such as methylene, ethylene, pentylene, propylene, isobutylene, t-butylene, 2-ethylpropylene and the like; and by m-phenylene, p-phenylene, 2,4-pyrrolylene, 3,4-pyrrolylene and like connecting groups.

When the compounds of formula IV are converted to the intermediates of formula III, they additionally comprise the Y group and the antibody moiety of the conjugates of formula I. Exemplary species of the antibodies and antibody fragments will be discussed below. When the Y group is a bond, the nature of the linkage is self-evident. When Y is of the formula E, exemplary species of Y are illustrated by the $R^2$ groups discussed immediately above, since $R^2$ is the only variable constituent of that Y linker.

When Y is a group of formula F, the following species are exemplary of it.

TABLE III

| $R^4$ | $R^3$ | $R^2$ |
|---|---|---|
| — | — | m-Phenylene |
| —$(CH_2)_4$— | —NH—CO— | p-Phenylene |
| —$CH_2(CH_3)_2C$— | —NH—CO— | 3,4-Pyrrolylene |
| — | — | 2,5-Pyrrolylene |
| — | — | 2,3-Pyrrolylene |
| —$CH(CH_3)CH_2$— | —NH—CO— | —$CH_2$— |
| —$CH_2$— | —NH—CO— | —$CH_2CH(CH_3)$— |
| — | — | —$C(CH_3)_2CH_2$— |
| —$(CH_2)_3$ | —NH—CO— | —$(CH_2)_5$— |
| —$(CH_2)_5$ | —NH—CO— | —$CH_2CH(CH_3)CH_2CH_2$ |

Finally, when the conjugates of formula I are completed by the reaction of the intermediates of formula II with the drug hydrazide, species of that aspect of the invention are exemplified by the various examples of the linker chemistry which have been described above, and by the various examples of the drugs which are described and exemplified in the section of this document which discusses the drugs in detail.

The conjugates of the present invention are composed of antibodies, certain cytotoxic drugs, and organic chemical groups which link antibody with drug. The invention also provides important intermediate compounds used for the preparation of the linking chemical groups. The antibodies and drugs will first be discussed individually, then the intermediates and their synthesis will be explained, and, finally, examples of the synthesis and biological performance of the conjugates will be shown.

THE ANTIBODY

It will be understood that the function of the present drug conjugates is determined by the biological efficacy of the drug and the antigenic selectivity of the antibody. An antibody is chosen which will recognize an antigen associated with a cell to which the particular drug is beneficially delivered. For example, if the drug is an antineoplastic, then an antibody which recognizes an antigen associated with tumor cells would be chosen. Depending on the characteristics of the drug to be used, it may be preferred in a given case to choose an antibody which is internalized by the cell, or it may be preferred to use an antibody which remains on the cell surface by recognizing a surface antigen.

The source of the antibody is not critical to the present invention. It may be chosen from any class or subclass of immunoglobulin including IgG, IgA, IgM, IgE and IgD. Similarly, the species of origin is not critical so long as the antibody targets a cell where the effect of the drug is useful.

In the present state of the art, monoclonal antibodies and their fragments are most used in drug conjugates, and use of them is preferred in the present invention. However, polyclonal antibodies and their fragments are not excluded. Newer types of antigen binding molecules can be produced by recombinant technology. See, e.g., Hodgson, Bio/Technology 9, 421–25 (1991).

Thus, chimeric and humanized antibodies of which one portion is derived from one species, and another portion is derived from another species may be obtained and used in the present invention.

The origin and nature of the antibody is not otherwise critical, so long as it targets the cell to be treated. Those of ordinary skill can readily prepare conjugates with a candidate antibody and evaluate them. Some discussion of the method of evaluating antibodies and conjugates will be provided for convenience. First, the antibody should be produced by a hybridoma or modified microorganism which is sufficiently stable to allow preparation of reasonable quantities of antibody. The antibody itself should be amenable to purification, and in particular should be sufficiently water-soluble to allow chemical manipulations at reasonable concentration.

Conjugates prepared with the candidate antibody are first evaluated for antigen-binding capacity. A modest reduction from the binding capacity of the free antibody is expected and acceptable. Then, the conjugate is tested to determine its in vitro potency, such as cytotoxicity in the case of anticancer drugs, against antigen positive cells. An effective conjugate can have potency somewhat less than the free drug in the same assay, because of its ability to bring a high concentration of drug to the cell. A conjugate which is accepted in the first two tests is then evaluated in a nude mouse human tumor xenograft model, as taught by Johnson and Laguzza, Cancer Res. 47, 3118–22 (1987). The candidate conjugate should be tested, for example, in nude mice against the free drug, a mixture of free drug and free antibody, and a conjugate with a nontargeting immunoglobulin, and should exhibit improved potency or safety over all. Dose ranging studies should be carried out in the xenograft model.

Conjugates which are potent in the xenograft model are submitted to tests in animals which are known to express the antigen of interest in a pattern similar to that seen in humans. If the conjugate produces a significant degree of binding to the antigen in such tests, and if it is reasonably free of toxicity at doses predicted by the xenograft model to be therapeutic, the candidate conjugate can be considered to have therapeutic potential.

It will be understood that properly chosen fragments of antibodies have the same effect as the intact antibody.

Thus, in the practice of this invention, fragments of antibodies, particularly F(ab')$_2$ fragments, which recognize an antigen associated with the cell to be treated, may be just as useful as are intact antibodies.

The mechanism by which the linker group reacts with and attaches to the antibody depends on the group Y in the linker. The linking mechanism of the Y group will be explained below in detail in the section on synthesis of the conjugates.

Formula I indicates that from 1 to about 10 linker-drug moieties are attached to each molecule of antibody. Of course, the number of such moieties per antibody molecule is an average number because a given batch of conjugate will necessarily contain molecules having a range of ratios of drug-linker to antibody. The most efficient use of the expensive antibody is obtained, of course, when a number of molecules of drug are attached to each antibody molecule. However, the attachment of an excessive number of molecules of drug-linker moiety usually has an adverse effect on the antibody's ability to recognize and bind to its antigen, so a compromise degree of substitution of the antibody must be found. When Y is carbohydrazide, the preferred substitution is by reverse proteolysis on the carboxy terminals, and therefore the number of carboxy terminals on the antibody defines the maximum possible degree of substitution.

A great number of antibodies are available to immunologists for use in the present invention, and further useful antibodies are being disclosed in every issue of the relevant journals. It is impossible, and entirely unnecessary, to give an exhaustive listing of antibodies which can be applied in the practice of this invention. Immunologists and chemists of ordinary skill are entirely able to choose antibodies from sources such as the catalogue of the American Type Culture Collection, Rockville, Md., U.S.A., and Linscott's Directory of Immunological and Biological Reagents, published by Linscott's Directory, 40 Glen Drive, Mill Valley, Calif., U.S.A., 94941. Thus, it is a simple matter for the artisan in the field to choose an antibody against virtually any determinant, such as tumor, bacterial, fungal, viral, parasitic, mycoplasmal, or histocompatibility antigens, as well as pathogen surface antigens, toxins, enzymes, allergens and other types of antigens related to physiologically important cells.

The most preferred use of the present invention is in the delivery of cytotoxic drugs to cancer cells, particularly including squamous carcinoma cells, adenocarcinoma cells, small cell carcinoma cells, glyoma cells, melanoma cells, renal cell carcinoma cells, transitional cell carcinoma cells, sarcoma cells, cells of supporting tumor vasculature, and cells of lymphoid tumors such as leukemias and lymphomas. Appropriate antibodies for the targeting of all such cells are available, and sources can be located in Linscott. Alternatively, the necessary hybridomas for the production of such antibodies by conventional methods are obtainable through ATCC and other cell line collections.

A number of presently known antibodies are particularly interesting for use in the anticancer aspect of the present invention. A preferred specific antibody, for example, is L/1C2, produced by ATCC hybridoma HB9682.

Another interesting antibody is KS1/4, first disclosed by Varki et al., Cancer Research 44, 681–86 (1984). A number of plasmids which comprise the coding sequences of the different regions of monoclonal antibody KS1/4 are now on deposit and can be obtained from the Northern Regional Research Laboratory, Peoria, Ill., U.S.A. The plasmids can be used by those of ordinary skill to produce chimeric antibodies by recombinant means, which antibodies bind to a cell surface antigen found in high density on adenocarcinoma cells. The construction of such antibodies is discussed in detail in U.S. Pat. No. 4,975,369. The following plasmids relate to KS1/4.

Plasmids pGKC2310, the coding sequence of the light chain, the signal peptide associated with the light chain, and the 5' and 3' untranslated regions; isolated from *E. coli* K12 MM294/pGKC2310, NRRL B-18356.

Plasmids pG2A52, the coding sequence of the signal peptide heavy chain, the coding sequence of the signal peptide associated with the heavy chain, and the 5' and 3' untranslated regions; isolated from *E. coli* K12 MM294/pG2A52, NRRL B-18357.

Plasmid CHKC2-6, the coding sequence of the light chain variable region, the coding sequence of the signal peptide associated with the light chain, and a sequence encoding the light chain constant region of a human IgG; isolated from *E. coli* K12 DH5/CHKC2-6, NRRL B-18358.

Plasmid CHKC2-18, the coding sequence of a derivative light chain variable region, the coding sequence of the signal peptide associated with the light chain, and a sequence encoding the light chain constant region of a human IgG; isolated from *E. coli* K12 DH5/CHKC2-18, NRRL B-18359.

Plasmid CH2A5, the coding sequence of the heavy chain variable region, the coding sequence of the signal peptide associated with the heavy chain, and a sequence encoding the heavy chain constant region of human IgG1; isolated from *E. coli* K12 MM294/CH2A5, NRRL B-18360.

Plasmid CH2A5IG2, the coding sequence of the heavy chain variable region, the coding sequence of the signal peptide associated with the heavy chain, and a sequence which encodes the heavy chain constant region of human IgG2; isolated from *E. coli* K12 DH5/CH2A5IG2, NRRL B-18361.

Plasmid CH2A5IG3, the coding sequence of the heavy chain variable region, the coding sequence of the signal peptide associated with the heavy chain, and a sequence encoding the heavy chain constant region of human IgG3; isolated from *E. coli* K12 DH5/CH2A5IG3, NRRL B-18362.

Plasmid CH2A5IG4, the coding sequence of the heavy chain variable region, the coding sequence of the signal peptide associated with the heavy chain, and a sequence encoding the heavy chain constant region of human IgG4; isolated from *E. coli* K12 DH5/CH2AIG4, NRRL B-18363.

Antibody 5E9Cll, produced by an ATCC hybridoma, HB21, recognizes transferrin receptor, which is expressed by many tumors. An antibody called B72.3, available from the National Cancer Institute, recognizes antigens expressed by both breast and colon carcinoma.

Two interesting antibodies with reactivities against non-tumor antigens are OKT3 and OKT4, which bind to peripheral T-cells and human T-helper cells, respectively. They are produced by hybridomas on deposit in the ATCC as CRL8001 and CRL8002, respectively.

Additional sources of antibodies useful for various therapeutic purposes are the following. Anti-human lymphocyte and monocyte antibodies, useful for immune modulation and tumor therapy, are produced by ATCC cultures HB2, HB44, HB78 and HB136. An anti-transferrin receptor antibody, useful for tumor therapy, is produced by ATCC culture HB84. ATCC culture HB8059 produces an antibody against colorectal carcinoma monosialoganglioside, and culture B8136 produces an antibody against mature human T-cell surface antigen, useful for immune modulation and T-cell leukemia therapy.

Still further, ATCC hybridoma HB9620 will produce a convenient anti-carcinoembyronic antigen called CEM231.6.7.

Schlom el al. have placed a number of interesting antibodies which have affinities for tumor-related antigens in the literature. In particular, the following articles and patents by that group are important.

Cancer Research 50, 1291–98 (1990)
Cancer Research 45, 5769–80 (1985)
International J. Cancer 43, 598–607 (1989)
U.S. Pat. No. 4,522,918
U.S. Pat. No. 4,612,282
European Patent Publication 0394277
European Patent Publication 0225709

The antibodies taught by the Schlom group which are functional in the context of the present invention include those with the designations D612, COL-1 through COL-15, CC-1, CC-8, CC-9, CC-11, CC-14, CC-15, CC-20, CC-26, CC-29, CC-30, CC-41, CC-46, CC-48, CC-49, CC-52, CC-55, CC-57, CC-60, CC-63, CC-66, CC-72, CC-74, CC-78, CC-83, CC-87, CC-90, CC-92.

An immunologist or one knowledgeable in the drug targeting art, with the assistance of the commonly known publications in the field and the above guiding examples and description, can readily choose an antibody for the targeting of any appropriate drug to any desired cell to be treated with that drug.

THE DRUG

It will be understood that the essence of the present invention is the method of linking drug and antibody by means of the linkers set out in formula I, and that neither the drug nor the antibody is a limitation of the present invention. The linkers of the present invention, accordingly, may be and are used beneficially with cytotoxic drugs of any type. In formula I, R is shown to be the residue of the drug, by which is meant the portion of the drug, terminating in a —CO— group, which possesses cytotoxic activity in either or both of the carboxy or carbonyl form, or the hydrazide form. Of course, it is necessary for the antibody to target a cell where the drug is beneficial.

The preferred drugs for use in the invention are those of the methotrexate class, and of the vinca class.

Such drugs can be described by the following structural formulae:

VINCA

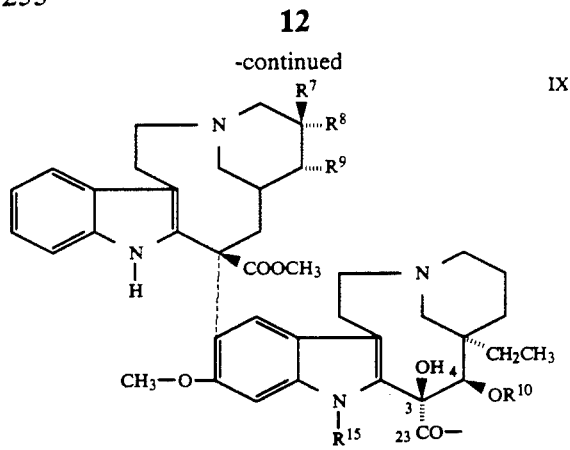

wherein $R^{15}$ is hydrogen, —$CH_3$ or —CHO; when $R^8$ and $R^9$ are taken singly, $R^9$ is hydrogen, and one of $R^7$ and $R^8$ is ethyl and the other is hydrogen or hydroxy; when $R^8$ and $R^9$ are taken together with the carbons to which they are attached, they form an oxirane ring in which case $R^7$ is ethyl; $R^{10}$ is hydrogen, ($C_1$-$C_3$alkyl)—CO—, or chlorosubstituted-($C_1$-$C_3$ alkyl)—CO—.

METHOTREXATE

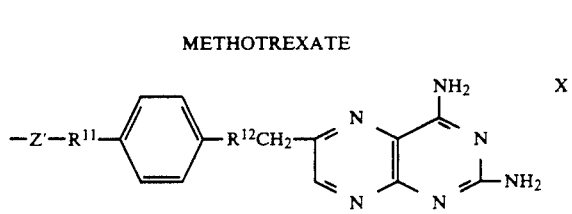

wherein
$R^{12}$ is $$-N-, -CH-,$$
$$\,\,\,\,\,\,\,\,R^{13}\,\,\,\,\,\,R^{13}$$

—S— or —O—;
$R^{11}$ is —CO—, —$SO_2$—, —CO—$(CH_2)_u$— or —CO—NH—;
$R^{13}$ is hydrogen or $C_1$-$C_3$ alkyl;
u is one or two;
Z' is

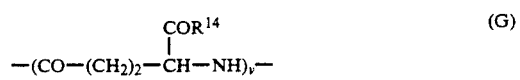  (G)

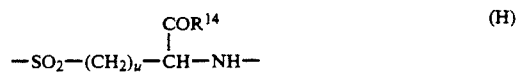  (H)

or

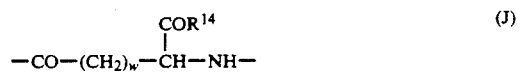  (J)

v is 1–6;
w is 1–22;
$R^{14}$ is hydroxy or a moiety which completes a physiologically-acceptable salt.

Further exemplary drugs are the verrucarins and the calicheamicins. The verrucarins are a family of macrocyclic tricothecane derivatives, originally produced by soil fungi. U.S. Pat. No. 3,087,859 is an early reference; Helv. Chim. Acta. 45, 840 (1962) teaches seven members of the family. *Merck Index*, 11th Ed., 1566 (1989) gives a bibliography. Patent Publication WO 9003401A1 teaches hydrazone derivatives. The structure of the verrucarins is exemplified by verrucarin A, which is shown below, in modified form, suitable for use as a drug in the present invention.

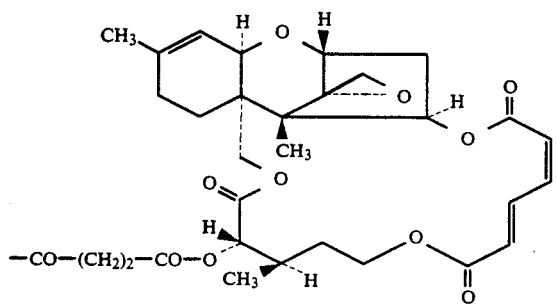

The calicheamicins are a new family of cytotoxic drugs. Maiese et al., J. Antibiotics XLII, 558-63 (1989). The complex structure of the compounds is represented by calicheamicin γ1, below; the molecule has been modified at the terminal sulfide linkage to make it appropriate for conjugate synthesis in the present invention.

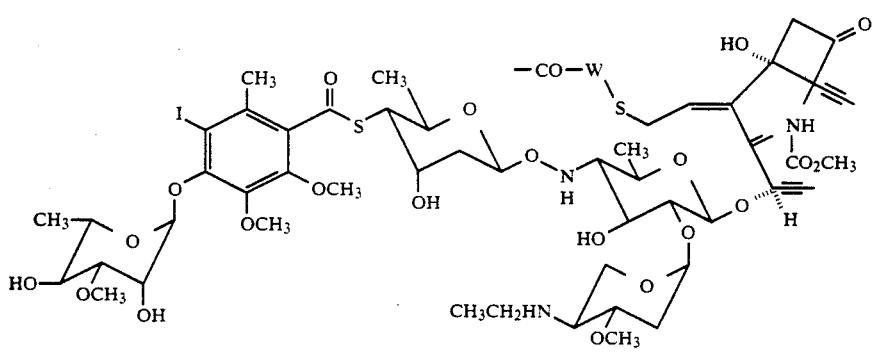

wherein W is phenylene or alkylene, such as ethylene, methylene, 1,1-dimethylethylene, isopropylene and the like.

Further members of the family differ in having one or two of the sugar moieties removed, or in having small acyl groups added.

The most highly preferred drugs are the vinca compounds of Formula IX above. It will be understood that the structural formula includes compounds which are, or are derivatives of, drugs having a number of different generic or trivial names. Accordingly, in order to simplify the complex nomenclature of the vinca drugs, they will be named in this document as derivatives of vinblastine. Vinblastine, it will be understood, is the compound of the formula above wherein $R^{15}$ is methyl, $R^7$ is ethyl, $R^8$ is hydroxy, $R^9$ is hydrogen, $R^{10}$ is acetyl, and the carbonyl group at $C_{23}$ is in the form of a methyl ester, rather than a carboxamide as shown above. The following table represents a number of vinca drugs which illustrate those used in the present invention.

TABLE IV

| $R^{15}$ | $R^7$ | $R^8$ | $R^9$ | $R^{10}$ |
|---|---|---|---|---|
| H | H | $C_2H_5$ | H | H |
| $CH_3$ | $C_2H_5$ | OH | H | H |
| CHO | $C_2H_5$ | H | H | $COCH_3$ |
| CHO | OH | $C_2H_5$ | H | $COC_2H_5$ |

TABLE IV-continued

| $R^{15}$ | $R^7$ | $R^8$ | $R^9$ | $R^{10}$ |
|---|---|---|---|---|
| $CH_3$ | $C_2H_5$ | Oxirane | | $COCH(CH_3)_2$ |
| H | $C_2H_5$ | H | H | $COCH_2Cl$ |
| $CH_3$ | $C_2H_5$ | Oxirane | | $COCHClCH_2Cl$ |
| H | $C_2H_5$ | Oxirane | | $COCCl_3$ |
| CHO | OH | $C_2H_5$ | H | $CO(CH_2)_2CHCl_2$ |
| $CH_3$ | H | $C_2H_5$ | H | H |
| $CH_3$ | $C_2H_5$ | OH | H | H |

The cytotoxic drug of formula X is methotrexate, aminopterin or a derivative thereof. The methotrexate drugs are used in the hydrazide form. The stereospecific forms of the various asymmetric centers of the drug are not indicated. Those of ordinary skill will understand that the stereochemistry of the drug may affect its activity, as is clearly explained in the art. The usual stereochemistry of the methotrexate drugs is preferably used in preparing intermediates for the present conjugates, but formula X includes all stereochemical forms.

The various groups which can vary in the drug of formula X will be discussed individually, and some preferred definitions of each will be given. It will be understood that preferred methotrexate drug hydrazides are made up of the preferred constituent groups, and pharmaceutical chemists, having knowledge of the pertinent literature, can prepare any such drug hydrazide.

The group $R^{12}$ is a bridging group which can be sulfur, oxygen, amino or methylene, the latter two of which may be optionally substituted with $C_1-C^3$ alkyl. Typical such groups are amino, methylene, methylamino, propylamino, 1,1-propylene and 1,1-isobutylene. The preferred $R^{12}$ groups are amino and methylamino.

The group $R^{11}$ is a bridging group which may be carbonyl, sulfonyl, acetyl, propionyl or carboxamido. In the latter three instances, the carbonyl group is adjacent to the group Z. The most preferred $R^{11}$ group is carbonyl, and acetyl and propionyl are also preferred.

The group Z' has an amino group at one end, which is attached to the group $R^{11}$, an has a carbonyl or sulfonyl group at the other end, which is attached to the =N—HN group. The Z group of formula G is derived from glutamic acid and, when t is not 1, constitutes the residue of polyglutamic acid. The preferred Z' group of formula G, however, is that wherein t is 1.

The Z' group of formula H terminates in a sulfonyl, and accordingly is the residue of the corresponding sulfonic acid. The group of formula H has one or two methylene groups, preferably two.

The Z' group of formula J is an amino acid of variable length, which may contain from 1 to 22 methylene groups. A preferred class of groups of formula J contains from 1 to 10 methylene groups, more preferably from 3 to 8 methylene groups.

The most preferred Z' groups are those of formula G, wherein v is 1, and those of formula J, wherein u is from 3 to 8.

In the groups of formula G, H and J, a carboxy group $R^{14}$ is present, in either free or salt form. The salts are formed with any moiety capable of forming a physiologically-acceptable salt of the carboxylic acid. Alkali metal and hydrohalide salts are particularly appropriate. Thus, the sodium, potassium and lithium salts, as well as the hydrochloride, hydrobromide and hydrofluoride salts, are particularly useful in the practice of the present invention. Other salts acceptable in pharmaceutical chemistry, however, are also useful. For example, amine salts such as triethylamine, triethanolamine, ethyldimethylamine and the like are useful, as are quaternary ammonium salts including tetraalkylammonium salts, (benzyl or phenyl)trialkylammonium salts and the like. Among ammonium salts, tetrabutylammonium, benzyltrimethylammonium, and tetramethylammonium are typical and preferred salts. Pharmaceutical chemists continually use salts of carboxylic acids, however, and the present salts, wherein $R^{14}$ is a salt-forming moiety, may be prepared with any base which forms a physiologically-acceptable salt.

The necessary intermediates from which to derive groups of formula X are in the pharmaceutical chemical art, and those of ordinary skill in that art can obtain any of them. A useful review artical on the synthesis of methotrexate drugs is Rahman and Chhabra, The Chemistry of Methotrexate and its Analogues, *Medicinal Res. Rev.* 8, No. 1, 95-155 (1988).

SYNTHESIS

It will be understood that the backbone of the compounds of the present invention is fundamentally made up of amino acids, which may be natural amino acids or may be somewhat modified. For example, an X group wherein t is 3 is a non-α amino acid. As has been pointed out, the various amino acid constituents may be in either the D or the L form, as discussed above.

The synthetic methods used to assemble the intermediates of formulae II-VI, and the final cytotoxic conjugates, as well as the modified drug of formula VIII, are fundamentally those which are conventionally applied in the synthesis of peptides from amino acid intermediates. It is conventional in such chemistry to block or protect various reactive functions on the starting compounds and intermediates while coupling reactions are carried out with other reactive functions After such a reaction is over, it is accordingly necessary to remove the protecting functions. Such protection and deprotection steps are entirely conventional in organic chemistry, and especially in peptide chemistry, and will not necessarily be explained in full in this document. It will be noted, however, that Greene's textbook on protective groups, cited above, fully explains protective groups for all of the reactive functions found on the intermediates used here, and outlines convenient methods for placing and removing those protective groups.

It will further be understood that the most convenient method for the preparation of amino acid constructions, such as the intermediates of the present invention, is by the use of an automated peptide synthesizer. Such tools are in common use, and have been described in the literature. Such peptide synthesizers are readily available; a well-known manufacturer of them is Applied Biosystems Inc., Foster City, Calif. 94404, (ABI), which sells an instrument known as the Model 430A.

The most convenient method of synthesis of all of the compounds of the present invention begins with the synthesis of an intermediate of formula VII.

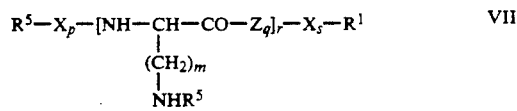

The synthesis of the above intermediate is illustrated below in Preparation 1, where such an intermediate is synthesized in an automated peptide synthesizer. The above intermediate is prepared from starting materials of formulae X and Z, and the amino acid below.

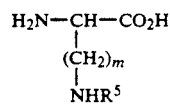

It will be understood that, when the synthesis of intermediate VII is carried out in a peptide synthesizer, the group $R^1$ represents the resin which is used in such chemistry to provide a substrate for the amino acid reactions.

The next step of the preferred process is to convert the intermediate of formula VII to the intermediate of formula VI, by reaction with an additional amino acid starting compound of the formula

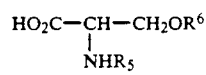

This reaction is conveniently carried out manually by conventional chemistry.

Next, if it is desired to provide an acyl spacer between the aminoxy group and the $X_p$ group, or to provide an aminoxyalkylene group, the appropriate steps are carried out. First, the $R^5$ protecting group is removed from the group $X_p$, by conventional means appropriate for the individual $R^5$ group. If an aminoxyacyl group such as the preferred aminoxyacetyl group is to be used, it may be provided by reaction with an appropriately protected derivative of aminoxyacetic acid, or any appropriate aminoxyalkanoic acid. In general, it will be necessary to use the acid in the form of an activated ester, most preferably as the N-succinimido ester. Thus, the intermediate of formula V is prepared. As shown in the examples and preparations below, that intermediate is used in the preparation of all of the cytotoxic conjugates of the present invention.

The direction of the synthesis, after the preparation of intermediate V, depends on the Y group to be used. If the Y group is to be merely a bond, then the conjugate of formula I is prepared by the direct reaction of the intermediate of formula V, in deprotected form, with a properly prepared antibody or antibody fragment. In this case, the link to the antibody or fragment is an oxime linkage, and the antibody is prepared by oxidizing it to obtain aldehyde functions on the carbohydrate portions of the antibody or fragment. Such reactions of antibodies have been extensively published in the past, for example, by McKearn et al., in European Patent Publication 088695 and U.S. Pat. No. 4671958; and Laguzza et al., European Patent Publication 247792.

Such reactions are carried out by oxidizing the desired antibody or antibody fragment with periodate, metaperiodate or another suitable oxidizing agent so that a bond between vicinal diols in a carbohydrate is ruptured to produce aldehyde groups on either side of the original bond. The number of dialdehyde units which are produced is a result of factors such as the amount of oxidizing agent, the time, temperature, solvent, and concentration of the oxidation, the number of vicinal diol carbohydrate units which are on the protein, and the steric accessibility of those diols to the oxidizing reagent. Alternatively, enzymatic oxidation with, for example, galactose oxidase may be employed. That reagent catalyzes the conversion of 6—$CH_2OH$ positions of galactose residues on the carbohydrate chains to an aldehyde functionality.

The oxidized antibody or antibody fragment is then reacted with the intermediate of formula V under conditions which are in general as illustrated in the examples below for reactions with antibody. The number of such reactions which occur on each molecule of antibody or antibody fragment can vary, in general, from one to about 10, and depends on the number of aldehyde groups on each antibody molecule, and upon steric effects. The reaction with intermediate V is carried out in an aqueous mixture, most preferably in a buffered aqueous solution which will not harm the antibody. A particularly appropriate aqueous medium is an acetate buffer, in which the concentration of acetate ion is about 0.1 molar. The pH of the reaction medium should be slightly acidic, in the range of about 4.5-6. Of course, because of the comparatively low solubility of antibodies, the concentration of the reaction mixture is usually quite low. The reaction temperature of the mixture is in the range from about 0° to about 40°, preferably from about 0° to about 25°, and reaction times up to 24 hours are usually adequate. Purification of the antibody conjugates will be discussed below, and is illustrated in the examples.

It will be understood that, in such a reaction, intermediate V is fully deprotected.

Alternatively, when Y is a group of formula E, the intermediate of formula V is converted to intermediate IV by reaction with an appropriate bis-aldehyde. For example, that intermediate, when $R^2$ is phenylene, is an $m$ or $p$ benzenedialdehyde, or is a pyrroldialdehyde such as pyrrol-2,5-dialdehyde, when $R^2$ is pyrrolyl. The intermediate may be an alkylenedialdehyde as well. As shown below in Example 4, the reaction is easily carried out at moderate temperatures in the range of from 0° to 50°, most preferably in aqueous buffer solutions, such as an acetate buffer at neutral or moderately acidic pH. Of course, the terminal amino group of intermediate V must be deprotected before the reaction is carried out, and the side chain protecting groups may be removed or not as is convenient in the circumstances.

The intermediate of formula IV is reacted with a carbohydrazide-modified antibody or antibody fragment. The carbohydrazide ($NH_2$—NH—CO—NH—$NH_2$) is reacted with the desired antibody or antibody fragment according to the teachings of Offord and Rose, European Patent Publications 359428 and 360433. The reaction is carried out in the presence of an appropriate protease, particularly endopeptidases, such as chymotrypsin or trypsin, or lysyl endopeptidase, or exopeptidases such as carboxypeptidase Y. Offord and Rose teach that such reactions result in the specific reaction of carbohydrazide with the terminal carboxy group or groups of the antibody or fragment, resulting in site-specific conjugation to the targeting agent. Thus, when an F(ab')-like antibody fragment is used, one or two linking groups may be attached to each molecule of antibody, and, when an F(ab')$_2$-like fragment or a complete antibody is used, up to four linking groups per molecule are possible.

The reaction to place the carbohydrazide on the antibody is characterized as a reverse proteolysis, which creates an imido bond, and is carried out under conditions which are generally appropriate for enzymatic reactions. An aqueous reaction medium should be used, which may constitute an aqueous buffer, and small amounts of water-miscible organic solvents, such as dimethylsulfoxide, dimethylformamide, acetonitrile and the like may be used as constituents of the mixture. In general, the reactions are carried out at temperatures near the ambient temperature, such as from about 0° to about 40°, at approximately neutral pH's, such as from about 4 to about 9.

Finally, in the preparation of conjugates of the type discussed, the carbohydrazide-modified antibody is reacted with the intermediate of formula IV under conditions much like those described above for reactions with oxidized antibody.

When the Y group is of formula F, the antibody is first acylated with the Y intermediate,

The intermediate should be preferably in the form of an activated ester, such as the N-succinimido ester, for best performance in the reaction. These intermediates, which preferably are amino acids wherein $R^3$ is —NH—CO— and $R^4$ is a small alkylene group such as an ethylene group, and wherein $R^2$ is most preferably pyrrolyl, are easily prepared by conventional methods in either the acidic or activated ester forms.

The reaction of the Y group intermediate and the antibody is conveniently carried out in aqueous media, similar to those which were described above under the heading of the reaction with oxidized antibody. In this case, the reaction is an acylation, where the activated carboxy group of the Y intermediate reacts, primarily, with amino groups of lysines of the antibody or antibody fragment. It is possible, however, that the acylation may also attack hydroxy groups, phenol groups, imidazole rings and perhaps other moieties of the antibody or fragment. Since numerous such groups are available on each Ab molecule, the number of acylations per Ab molecule is not fixed, but may be controlled by concentration of the reactants, temperature, time of the reaction and other factors which are commonly understood. As many as about 10 acylations per Ab molecule may occur, as pointed out in the definition of the compounds of formula I above.

The above reactions with antibodies or modified antibodies provide intermediates of the type of formula III, wherein the antibody and —Y=linking group are in place, and the side chain of the intermediate is fully deprotected.

The intermediate of formula III is converted into the intermediate of formula II by oxidation. Such an oxidation is illustrated in Example 6 below, and is readily carried out with oxidizing reagents such as periodate, metaperiodate and the like. Aqueous reaction mixtures are appropriate, particularly plain water. It is advisable to use a modest excess of oxidizing reagent, such as from 2- to 10-fold excess. The concentration of the reaction mixture will necessarily be quite low, because of the limited solubility of antibody. The oxidation is very quick and reaction times in the range of from a few minutes to an hour have been found to be adequate. When the oxidation is complete, or as complete as is desired, the excess oxidizing reagent is quenched by the addition of ethylene glycol as an aqueous solution, and the intermediate of formula II is then purified by chromatography as discussed below.

The final step of the preparation of the conjugates of formula I is the reaction of the intermediate of formula II with the drug hydrazide. The drugs used in the present invention are discussed in detail above. As explained there, the drugs are in the hydrazide form in order to be useable in the present invention. Reaction of the intermediate of formula II with the drug hydrazide is conveniently carried out in aqueous buffer, of which a dilute acetate buffer has been found to be preferred. Again, the concentration of the reaction mixture must be comparatively low, to accommodate the antibody's solubility, and the reaction with the drug is most conveniently carried out at pH's in the range of from about 4 to about 7. It is advisable to use a considerable excess amount of drug hydrazide, at least 5-fold excess, and the reactions have been found to be comparatively slow. Twenty-four hours or even more of reaction time is sometimes necessary. Of course, the reactions with the drug hydrazides must be carried out at gentle conditions, typically at from about 0° C. to about ambient temperature, in order to protect the fragile antibody in this comparatively lengthy reaction.

Finally, the product of formula I is purified, and it may be advisable to purify the various intermediates in the course of the multiple-step process. The reader is asked to refer to the preparations and examples below for insight into the appropriate purification measures. It will be understood, of course, that there is no one best purification process, but that the purification must be adjusted to suit the particular intermediates and product being prepared. In general, purification is carried out by dialysis and chromatographic procedures. Dialysis, as in stirred cells, into phosphate buffered saline or a similar low-concentration buffer is a particularly convenient method for concentration of products and intermediates which are prepared in very dilute reaction mixtures. High performance, high pressure liquid chromatography is the generally preferred purification process, a wide variety of media for which are made by companies such as Pharmacia. The product literature produced by such manufacturers should be consulted, but the chromatographic purification of these products is not dissimilar to the purification of numerous other protein-based substances. The product-containing fractions of chromatography operations may be identified, and the concentrations of the intermediates and products measured, by ultraviolet spectroscopy, as protein products have often been analyzed in the art.

The synthesis of the modified drug of formula VIII is carried out in the same manner, substantially, as has just been described, up to the preparation of the intermediate of formula VI. That intermediate is then de-protected at the side chain groups, and is oxidized as described above in the discussion of the synthesis of the intermediate of formula II. The oxidized intermediate corresponding to formula VIII is then reacted with the drug hydrazide to prepare the desired product of formula VIII. The $R^1$ and $R^5$ protecting groups may be removed or left in place, as is preferred in the circumstances.

The following preparations and examples further illustrate the manner in which the compounds of the present invention are prepared. It will be understood, of course, that the following preparations and examples may be used as guides to the skilled artisan in the preparation of all of the compounds described in the present document.

The nomenclature of the linker intermediates and the linker portions of the conjugates is quite difficult. Accordingly, in most cases below the identity of the linker intermediates will be indicated by a structural formula, in order to avoid the extremely complex nomenclature problems.

PREPARATION 1

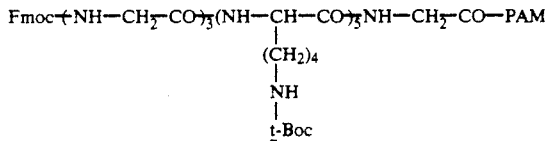

In the above structure, Fmoc refers to the 9-fluorenylmethoxycarbonyl protecting group, *t*-Boc refers to the *t*-butoxycarbonyl protecting group, and PAM refers to phenylacetamidomethyl resin, obtained from ABI.

A 0.5 mmol portion of *t*—BOC—NH—CH$_2$—CO—PAM was used as the starting material for the synthesis of the above-described nonapeptide, making use of an ABI 430A automated peptide synthesizer, using the Fmoc protocol. Each cycle of the synthesis was controlled by ninhydrin analysis, and it was found that the coupling at each cycle was essentially quantitative. The yield was 1.13 g of the desired intermediate, in resin-bound form.

EXAMPLE 1

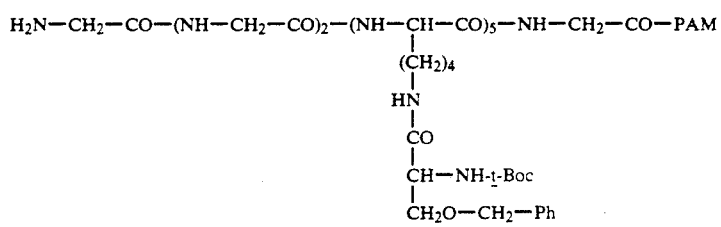

In the above structure, the term Ph refers to the phenyl group.

The intermediate made in Preparation 1 above was treated with 40 ml of trifluoroacetic acid for one hour, and the intermediate was then filtered, washed with dichloromethane, and dried. A 1.96 g portion of serine, which carried a benzyl protecting group on the hydroxy, a *t*-butoxycarbonyl protecting group on the nitrogen, and a N-hydroxysuccinimido group on the carboxyl group, was dissolved in 5 ml of dimethylsulfoxide, and the apparent pH of the solution was brought to 8 by addition of N-methylmorpholine. The deprotected intermediate of Preparation 1 was added to the solution, and the apparent pH was readjusted to 8. The mixture was agitated in the dark at ambient temperature for 20 hours, filtered, and the precipitate was washed with 10 ml of dimethylsulfoxide, three times with 20 ml portions of methanol, and three times with 20 ml portions of dichloromethane. The yield was 1.15 g of the desired intermediate. The resin was then treated for 3 hours with a mixture of 2 ml of piperidine and 2 ml of dimethylformamide with strong agitation to remove the Fmoc group, and the resin was then filtered, washed three times with 10 ml portions of dichloromethane and dried. The yield was 0.95 g of intermediate.

PREPARATION 2

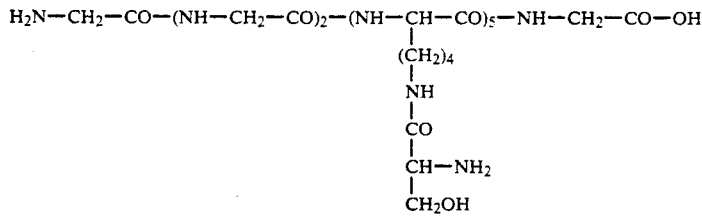

A 100 mg portion of the intermediate of Example 1 was deprotected and cleaved from the resin by treatment first with 1 ml of trifluoroacetic acid for 30 minutes. Then 100 μl of trifluromethanesulfonic acid was added and the mixture was stirred vigorously for 60 minutes. Then 4 ml of diethyl ether was added, and the precipitate was recovered in the presence of the cleaved resin by centrifugation, and washed three times with 4 ml portions of diethyl ether. The peptide was then recovered by dissolution in 3 ml of water and filtration on a 0.2μ filter to remove resin particles, and identified by high performance liquid chromatography on a Waters instrument with WISP automatic sample injector. The column was 250 mm × 4 mm, of Machery Nagel Nucleosil 300A 5 μm C8 medium, injecting at 0.6 ml/minute. The eluting solvent was a gradient, beginning with solvent A (1 g/liter trifluoroacetic acid) for 5 minutes, and then adding solvent B (1 g/liter trifluoroacetic acid in 90% aqueous acetonitrile) at 2%/minute to 100% B. The absorbance was monitored at 214 mm. The major component was purified by chromatography isocratically with 100% solvent A, and shown to be consistent with the above desired nonapeptide. The yield was about 26 mg.

EXAMPLE 2

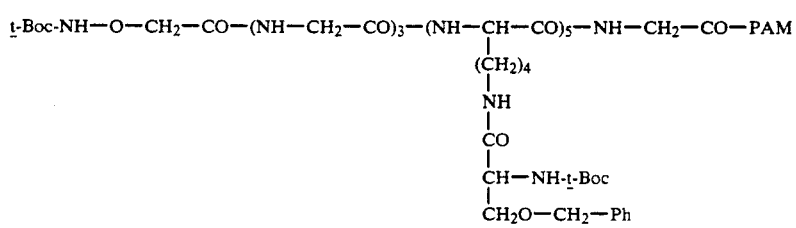

A 300 mg portion of the intermediate prepared in Example 1 above was acylated by reaction with 3.3 millimoles of N-*t*-butoxycarbonylaminooxyacetic acid, N-hydroxy-succinimido ester, in 8 ml of dimethylsulfoxide at ambient temperature and pH 8. The mixture was stirred for 18 hours, and the resin was then filtered, washed with 3, 10 ml portions each of dimethylsulfoxide, methanol, and dichloromethane, and dried in a desiccator under vacuum to obtain 247 mg of the desire intermediate.

EXAMPLE 3

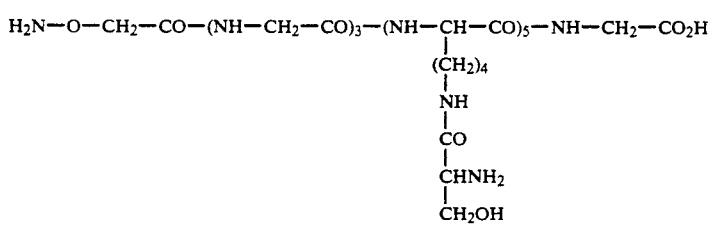

A 100 mg portion of the intermediate of Example 2 was treated with 3.5 ml of trifluoroacetic acid for 1 hour. The resin was then filtered, washed 5 times with 10 ml portions of dichloromethane and dried under vacuum. A 50 mg portion of the treated resin was then cleaved by adding 0.5 ml of trifluroacetic acid, mixing for 15 minutes, and adding 50 μl trifluoromethanesulfonic acid and mixing vigorously for 30 minutes more.

Four ml of diethyl ether was then added, and the precipitate was recovered by centrifugation and washed 3 times with 4 ml portions of diethyl ether. The precipitate was then taken up in 4 ml of water, and filtered through a 0.2 μm filter to remove resin particles; yield on evaporation was 14.9 mg of white solid. The components were separated by chromatography substantially as shown in Preparation 2 above, and the major component was collected and found by positive ion fast atom bomdardment mass spectroscopy (FAB-MS) to be consistent with the desired intermediate. The yield was 3.4 mg.

EXAMPLE 4 at 37°, and the reaction is stopped when 80% of the original antibody has been digested, after 4-8 hours. The reaction is then halted by adding 1M triethanolamine to a final concentration of 50 mM in the reaction mixture and adjusting the pH to 8.0 with dilute sodium hydroxide. The antibody fragment is then purified by first diluting the reaction mixture with two volumes of 170 mM acetic acid, at pH 4.5 and adjusting the diluted mixture to 4.5 with additional acetic acid. A precipitate forms, and the mixture is then clarified by centrifuging it for 20 minutes at 20,000 xg. The clarified mixture is then chromatographed on a S-Sepharose FF column, eluting first with 170 mM acetic acid, pH 4.5, and then with a linear gradient, proceeding from the above elu-

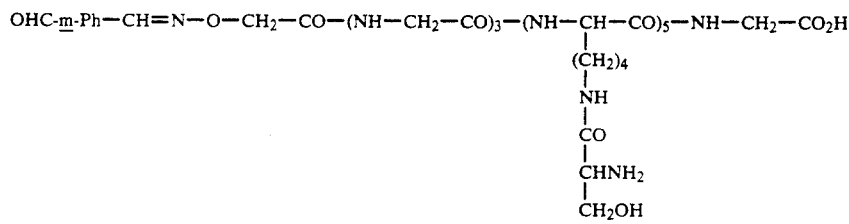

To 300 μl of a solution in water (29 nmol/μl) of the intermediate prepared in Example 3 above was added 1.2 ml of a solution of isophthalaldehyde (13.4 mg dissolved in 0.5 ml acetonitrile to which 2 ml 0.1M sodium acetate buffer at pH 4.6 was added). The reaction mixture was stirred at ambient temperature (22° C.) for 90 minutes, and the product was isolated by reversed phase HPLC as described for preparation 2 except that a flow rate of 1 ml/min was used. The sample was applied in 5 runs of 300 μl. For each run, after injection at 100% solvent A, elution was with 100% A for 5 min, followed by 1.75% B/min for 4 minutes, followed by isocratic 7% B for 10 minutes, followed by 1% B/min for 30 min, monitoring at 214 nm. Excess isophthalaldehyde eluted as the first major peak, and product eluted as the second major peak. Evaporation of the pooled product peaks gave 5.25 mg product, identified by FAB-MS.

PREPARATION 3

Peptic F(ab')₂ Fragments of Antibody 007B

Antibody 007B is produced by a hybridoma which is a subclone derived from the hybridoma producing the antibody KS1/4, which is discussed above in the antibody section of this document. F(ab')₂ fragments of antibody 007B are prepared by digesting antibody 007B with pepsin. First, a solution of antibody 007B in 1% acetic acid is prepared, at a concentration between 5 and 10 mg of antibody per ml. The pH of the solution is then adjusted to 4.2-4.3, and the solution is then warmed to 37°. To it is added a solution of pepsin in 1% acetic acid, at a concentration between 10 and 20 mg/ml. The ratio between the amount of pepsin and the amount of antibody is 0.03. The mixture is gently stirred ant to 250 mM sodium chloride in the first eluant. The 007B fragment-containing fractions from the chromatography are identified by UV analysis at 280 nm and by SDS-Page gel. The product-containing fractions are pooled, and triethanolamine is added to a final concentration of 50 mM, after which the pH is adjusted to 7.4. The antibody fragment product is then concentrated by ultrafiltration.

PREPARATION 4

Carbohydrazide Derivative of Achromobacter-derived Antibody 007B F(ab')₂ Fragment A 12.4 g portion of carbohydrazide was dissolved in water and the pH and volume were adjusted by addition of water and acetic acid to obtain 50 ml of solution at pH 5.5. A 815 μl portion of this solution was added to 16.3 mg of F(ab')₂ fragment of antibody 007B, at ambient temperature, and 81 μl of a 10 mg/ml solution of Achromobacter protease was added. The mixture was stirred gently from time to time at ambient temperature for 3 hours. The 106 μl of a 78 mg/ml solution of Kallikrein trypsin inhibitor (Bayer) was added, and the mixture was applied to a Superose 12 column (Pharmacia), and run in a buffer of 0.1M sodium acetate at pH 4.6. The product-containing fractions, as identified by absorbance at 300 nm, were pooled and concentrated to about 200 μl volume. The process was carried out twice and the products were pooled to obtain about 15.9 mg of the desired product, in which carbohydrazide is reacted with and linked to the terminal carboxy groups of the antibody fragments.

EXAMPLE 5

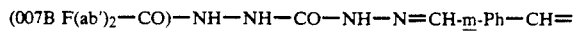

-continued

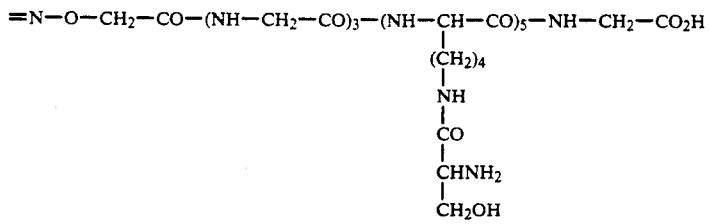

To 410 μl of the modified antibody of Preparation 4 was added 7.9 μl of the intermediate of Example 4 as a 151 mg/ml solution in water. The mixture was gently stirred and held at ambient temperature for 20 hours, and was then loaded onto a Superose 12 HR 10/30 column equilibrated and eluted with 0.1M sodium acetate buffer at pH 4.6. The protein peak was concentrated and reapplied to the Superose column, equilibrated and eluted with 50 mM imidazole, adjusted to pH 6.95. The F(ab')₂-sized material was concentrated to 400 μl to obtain about 8.9 mg of the desired intermediate.

EXAMPLE 6

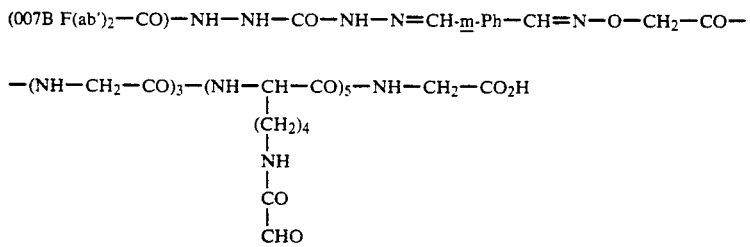

To the intermediate prepared in Example 5 above was added 17.8 μl of a solution of sodium metaperiodate in water, containing 22.8 mg/ml. The mixture was gently stirred for 5 minutes at ambient temperature, and the oxidation was then stopped by the addition of 17.8 μl of a solution of ethylene glycol, containing 11.2 μl/ml in water. The reaction mixture was then loaded onto a Superose 12 HR 10/30 column, equilibrated and eluted with 0.1M sodium acetate at pH 5.6. The protein-containing peak was concentrated to 380 μl to obtain about 8.6 mg of the desired product.

EXAMPLE 7

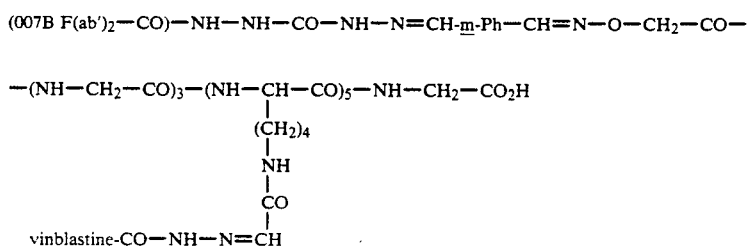

In the above structural formula, the term —CO—vinblastine refers to the vinca drug vinblastine, linked through the $C_{23}$ carbonyl group, at the 3-position of the vinca nucleus.

To the intermediate prepared above in Example 6 was added 86.3 μl of a solution containing 0.1M 4-desacetyl-23-desmethoxyvinblastine-23-hydrazine in 0.1M sodium acetate at pH 5.6. The reaction mixture was incubated for 18 hours at ambient temperature, and was then dialyzed at 4° against 50 mM sodium dihydrogenphosphate buffer containing 0.1M sodium chloride at pH 7. The product, recovered as a precipitate, was dissolved in phosphate buffered saline containing 0.2% Sarcosyl, (sodium lauryl sarcosinate).

The product was identified by ultraviolet spectroscopy at 280 and 320 nm.

EXAMPLE 8

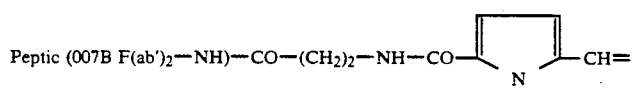

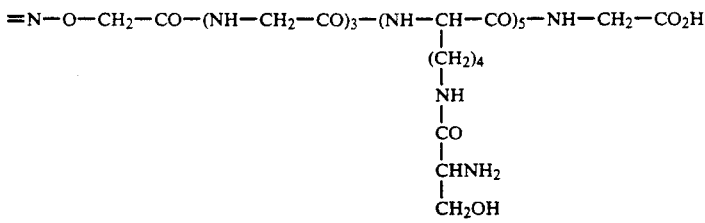

A 20 mg portion of antibody 007B F(ab′)₂ fragment, prepared as in Preparation 3, was solvent exchanged into 0.34M sodium borate buffer, at pH 8.6, to a concentration of 23.2 mg/ml. To this solution was added 28 μl of an acetonitrile solution of 3-(5-formylpyrrol-2-ylcarbonylamino)propionic acid, N-hydroxysuccinimide ester, at a concentration of 4.3 mg/ml. The mixture was stirred at ambient temperature for 1 hour, and it was then concentrated by dialysis in a stirred cell with a 10,000 molecular weight cut off membrane, dialyzing into sodium acetate buffer at pH 5.6. The product solution contained 16.5 mg of the 3-(5-formylpyrrol-2-ylcarbonylamino)propionyl derivative of antibody 007B fragment, in the form of 1.44 ml of solution containing 11.5 mg/ml. The conjugation ratio of the product was 1.5 moles of formylpyrrol linker per mole of antibody fragment, as determined by UV spectroscopy, measuring absorbance at 300 and 280 nm.

Half of the above intermediate, 0.72 ml of the product solution, was combined with 0.57 mg of the intermediate of Example 3 above, as a solid, and the mixture was stirred at ambient temperature for 24 hours. It was then filtered through an 0.2 μm membrane filter, and was then purified by solvent exchange in a stirred cell into pH 6.9 imidazole buffer. The product was concentrated to near dryness, 2 ml of imidazole buffer was added, and the solvent exchange process was repeated twice. The product was identified as the desired intermediate shown in the structure above, in the form of 1.44 ml of solution containing 5.8 mg of product.

EXAMPLE 9

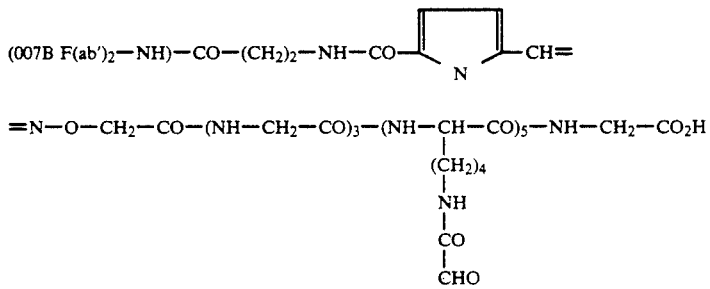

The product of Example 8 was combined with 31 μl of 5 mg/ml sodium metaperiodate in imidazole buffer, and the oxidation reaction was carried out and quenched with ethylene glycol substantially as shown in Example 6 above. The reaction mixture was purified by solvent exchange into sodium acetate buffer at pH 5.6 in a stirred cell, to obtain 1.5 ml of product solution containing 5.4 mg of the desired product, as determined by UV analysis at 300 and 280 nm.

EXAMPLE 10

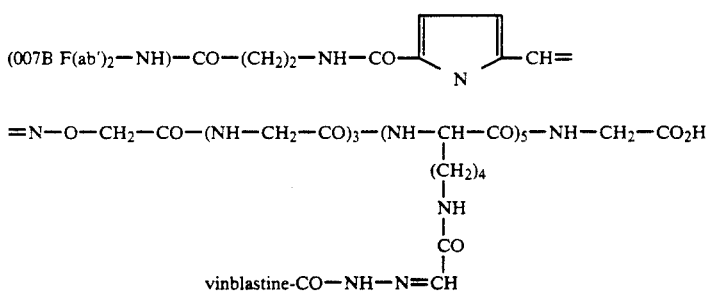

To the product of Example 9 was added 6.5 mg of 4-desacetyl-23-desmethoxyvinblastine hydrazide, as a solid, and the mixture was stirred at ambient temperature for 36 hours. The mixture was then centrifuged for 10 minutes to clarify it, and it was chromatographed over a 26×1.5 cm Sephadex G-25 (Pharmacia) column, eluting with phosphate buffered saline at pH 7.4. The product-containing fractions were combined and filtered through a 0.2 μm membrane filter, to obtain 3.16 ml of solution containing 1.43 mg of the desired product. Analysis of the product by ultraviolet spectroscopy, measuring absorbance at 270 and 280 nm, showed that the product contained 8 moles of vinblastine per mole of antibody fragment.

EXAMPLE 11

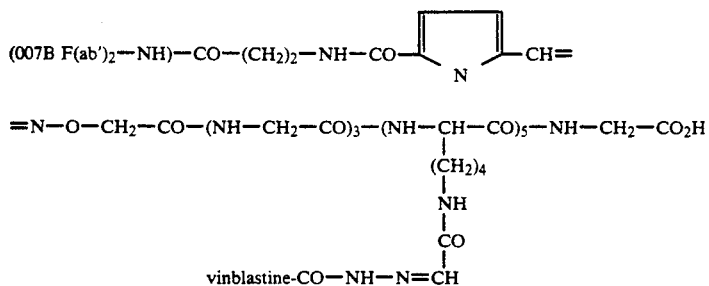

Another synthesis of the product of Example 10 was carried out, starting with 100 mg of F(ab')2 fragment of antibody 007B and 0.61 mg of 3-(5-formylpyrrol-2-ylcarbonylamino)propionic acid, N-hydroxysuccinimide ester, and 103 mg of the acylated antibody was obtained at a conjugation ratio of 1.3 moles of linker per mole of antibody fragment. To that intermediate was added 7.2 mg of the intermediate of Example 3, and the reaction was carried out as shown in Example 8. A yield of 91.3 mg of that intermediate was obtained, as 12.8 ml of solution in imidazole buffer at pH 6.95.

That intermediate product was oxidized with sodium metaperiodate as described in Example 6 to obtain 89.3 mg of oxidized intermediate, as described in Example 9, in the form of 13.3 ml of solution. To it was added 57.6 mg of 4-desacetyl-23-desmethoxyvinblastine hydrazide sulfate, and the reaction mixture was stirred overnight at ambient temperature. The mixture was then purified by chromatography as described above in Example 10 to obtain 80 mg of the desired product in the form of 24.9 ml of solution in phosphate buffered saline. The conjugation ratio was determined to be 5.3 moles of vinblastine per mole of antibody fragment, as determined by analysis as described above in Example 10. The product was concentrated by stirred cell and filtered through an 0.2 μm membrane filter, to obtain 65 mg of the product in the form of 10.9 ml of a 6 mg/ml solution in phosphate buffered saline. The conjugation ratio was 5.0 moles of vinblastine/mole of 007B fragment.

A precipitate which formed in the product after standing at 4° for 3 days was removed by 0.2 μm filtration to yield 63 mg of the product in the form of 10.2 ml of a 6.2 mg/ml solution, with a conjugation ratio of 3.9 moles/mole.

The product was compared with unmodified antibody fragment to determine its ability to bind P3-UCLA carcinoma cells. Binding was determined by measurement of immunofluorescence, and it was determined that the product had 78% of the binding power of the native antibody fragment. Thus, it was clear that the conjugated antibody was still effective in binding to carcinoma cells.

The cytotoxicity of the conjugated product of this example was also determined, in comparison with desacetylvinblastine hydrazide, in P3-UCLA cells. The 50% inhibitory dose of the product of this example was 0.017 μg/ml, and the corresponding dose of the unconjugated vinca drug was less than 0.001 μg/ml.

EXAMPLE 12

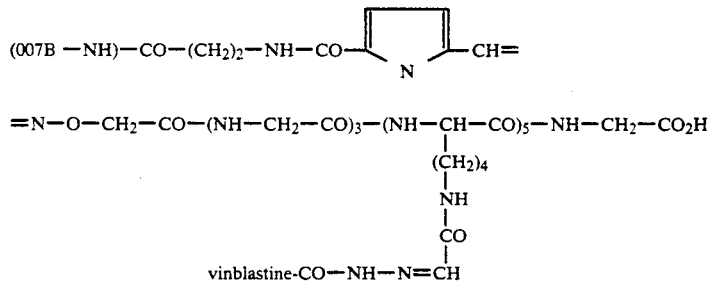

A 10 mg portion of antibody 007B was dialyzed into 1 ml of 0.34M borate buffer at pH 8.6, and was reacted with 0.1 mg of 3-(5-formylpyrrol-2-ylcarbonylamino)-propionic acid, N-hydroxysuccinimide ester, which was added in 24 μl of acetonitrile. The reaction mixture was stirred 1 hour at ambient temperature, and was purified by chromatography on a Sephadex G-25 column, eluting with 0.1M sodium acetate buffer at pH 5.6. The product-containing fractions were filtered through an 0.2 μm membrane filter to obtain 6.2 mg of the 3-(5-formylpyrrol-2-ylcarbonylamino)propionyl derivative of the antibody. The conjugation ratio was 2.7 moles of the linker per mole of antibody.

The product solution was concentrated in a stirred cell, to obtain 0.9 ml of derivatized antibody solution at a concentration of 6.4 mg/ml. To it was added 0.67 mg of the intermediate of Example 3, and the mixture was stirred at ambient temperature overnight. The reaction mixture was then purified and solvent exchanged into pH 6.9 imidazole buffer using a stirred cell with a 30,000 molecular weight cut off membrane.

The product solution consisted of 1.4 ml, containing 5.2 mg of product corresponding to that of Example 8, except that the antibody is 007B instead of 007B F(ab')2.

That product was oxidized with sodium metaperiodate, and the reaction was quenched with ethylene glycol, substantially as described in Example 6, to obtain 4.6 mg of oxidized product, corresponding to that of Example 9 above, as a solution in 0.1M sodium acetate buffer at a concentration of 2.3 mg/ml.

To the solution was added 8.67 mg of 4-desacetyl-23-desmethoxyvinblastine hydrazide sulfate, and the mixture was stirred overnight at ambient temperature. The reaction mixture was centrifuged, and then purified by chromatography on a Sephadex G-25 column, eluting with phosphate buffered saline at pH 7.4. The product-containing fractions were combined and found to contain 2.2 mg of the desired product, in the form of 5.3 ml of solution. Analysis by ultraviolet spectroscopy showed that the conjugation ratio was 12 moles of vinblastine per mole of antibody.

The ability of the conjugate to bind to P3-UCLA cells was compared to unmodified antibody. It was found that the binding potency was 84% of that of the unmodified antibody, indicating strong ability to bind carcinoma cells.

Cytotoxicity of the product of this example against P3-UCLA cells was determined, and it was found that the 50% inhibitory dose was 0.027 μg/ml, compared to 0.003 μg/ml for free desacetylvinblastine hydrazide.

EXAMPLE 13 mediate, of which 14.3 mg was obtained in the form of 4.1 ml of solution, was reacted with 17.6 mg of 4-desacetyl-23-desmethoxy-vinblastine hydrazide sulfate. The reaction mixture was purified by chromatography over Sephadex G-25, eluting with pH 7.4 phosphate buffered saline, and the product-containing fractions were combined to obtain 2.4 mg of the desired product, in the for of 7.6 ml of solution. Analysis by ultraviolet spectroscopy, measuring absorbance at 270 and 280 nm, indicated a conjugation ratio of 23 moles of vinca drug per mole of antibody.

EXAMPLE 14

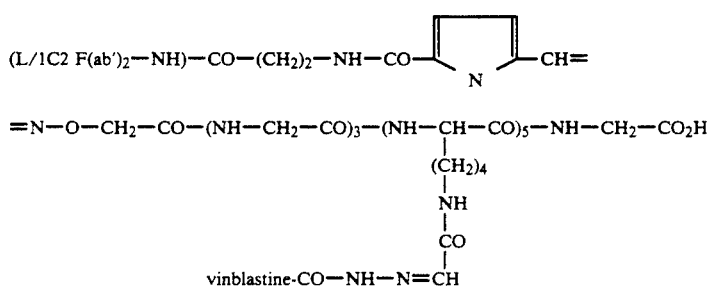

Antibody L/1C2 is prepared by culturing the L/1C2 hybridoma, which is obtained from the American Type Culture Collection under the accession number HB9682. Viable cells are recovered by thawing the contents of a vial in a 37° C. water bath while swirling the vial. The cell suspension is then diluted 1:2 with balanced salt solution (Grand Island Biological Company (GIBCO), 3175 Staley Road, Grand Island, N.Y. 14072) and the suspension is centrifuged through a

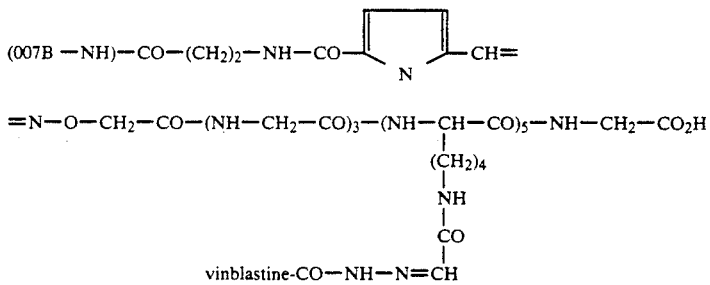

A 25.8 mg portion of antibody 007B was reacted with 0.42 mg of 3-(5-formylpyrrol-2-ylcarbonylamino)propionic acid, N-hydroxysuccinimido ester, as described in Example 12 above. Concentration of the reaction mixture provided 18.7 mg of derivatized antibody, having 4.2 moles of linker groups per mole of antibody, in the form of 2.8 ml of solution. That product was reacted with 3.6 mg of the intermediate of Example 3, which was added as a solid and stirred at ambient temperature overnight. The reaction mixture was then concentrated and purified by Sephadex G-25 size exclusion chromatography into imidazole buffer at pH 6.9 to obtain 16.4 mg of product, corresponding to that of Example 8 above, but based on antibody 007B instead of the F(ab')$_2$ fragment, in the form of 6.5 ml of solution. Analysis by ultraviolet spectroscopy, measuring absorbance at 280 and 300 nm, indicated a linker conjugation ratio of 4.6 at that stage.

That product was oxidized with sodium metaperiodate, as described in Example 6, and the oxidized interserum underlay to partition the cells from the cryogenic medium. The supernatant is aspirated, and the cells in the cell pellet are suspended in culture medium (Ventrex HL-1, Ventrex Laboratories, Portland, Me.) supplemented with 10% fetal calf serum, 2 mM L-glutamine (GIBCO) and 50 μg/ml gentamicin sulfate (GIBCO)) in T75 tissue culture flasks, in 5% carbon dioxide at 37° C. Supernatants from nearly confluent cultures are collected and residual cells are removed by centrifugation. Antibody is purified from the cell free supernatant by passing over a Protein A Sepharose column (Pharmacia). Antibody binds to the column and culture medium is washed free in 0.01M sodium phosphate at pH8.0. Antibody is then eluted from the column with 0.1M sodium phosphate buffer at pH 3.5. Eluted antibody is immediately neutralized with 1M Trizma buffer (Sigma, St. Louis, Mo.) at pH 7.4 and dialyzed and concentrated in a vacuum dialyzer (Bio-Molecular Dynamics, Beaverton, Oreg.) containing 0.01M sodium phosphate pH 7.4 plus 0.15M sodium chloride. Antibody preparations are sterilized by filtration through 0.2 μm pores and stored at 4° C. until used.

The F(ab')₂ fragment of antibody L/1C2 is prepared by adding 2.4 ml of pepsin solution, containing 12.6 mg of pepsin/ml, to 1.5 g of L/1C2 antibody in 270 ml of phosphate buffered saline. The mixture is held at 37° for 2 hours and 20 minutes, and then the reaction is stopped by the addition of triethanolamine. The product is then concentrated by chromatography on a Sepharose Fast Flow column, eluting with 0.15M sodium acetate. The F(ab')₂-containing fractions are combined, and concentrated by dialysis to obtain 100 ml of product solution containing 992 mg of the F(ab')₂ fragment of antibody L/1C2.

A 20 mg portion of F(ab')₂ fragment of antibody L/1C2, in 0.8 ml of 0.34M borate buffer at pH 8.6, was reacted with 0.12 mg of 3-(5-formylpyrrol-2-ylcarbonylamino)propionic acid, N-hydroxysuccinimido ester, which was added as 28 μl of solution in acetonitrile. The mixture was stirred one hour at ambient temperature, and was then solvent exchanged into 0.1M sodium acetate buffer at pH 5.6 in a stirred cell, using a 30,000 molecular weight cut off membrane. A yield of 15.4 mg of derivatized antibody was obtained, in the form of 1.3 ml of solution. Analysis by ultraviolet spectroscopy indicated 1.6 moles of linker per mole of antibody fragment.

To the product solution was added 1.1 mg of the intermediate of Example 3, and the mixture was stirred overnight at ambient temperature. It was then purified in a stirred cell and simultaneously solvent exchanged into imidazole buffer at pH 6.95. The product consisted of 12.8 mg, corresponding to that of Example 8 but with L/1C2 instead of antibody 007B, in the form of 1.9 ml of solution in imidazole buffer.

That product was oxidized with sodium metaperiodate, substantially as described in Example 6, to obtain 12.0 mg of oxidized product in the form of 2 ml of solution in 0.1M sodium acetate buffer at pH 5.6.

A 5.4 mg portion, corresponding to 0.9 ml of solution, of the above product was reacted with 3.9 mg of 4-desacetyl-23-desmethoxyvinblastine hydrazide sulfate, and the product was purified and isolated as described in Example 10 to obtain 3.9 mg of the desired product, in the form of 2.7 ml of solution in phosphate buffered saline. The conjugation ratio was determined to be 7.2 moles of vinblastine per mole of antibody fragment.

EXAMPLE 15

A 5.4 mg portion of the oxidized intermediate from Example 14 above was combined with 2.5 mg of methotrexate-γ-hydrazide and the mixture was stirred overnight at ambient temperature. The reaction mixture was then purified by size exclusion chromatography on Sephadex G-25, and filtered through a 0.2 μm membrane to obtain 5.4 mg of the desired product, as 3.3 ml of solution in phosphate buffered saline. UV analysis at 260 and 280nm showed the conjugation ratio to be 4 moles of methotrexate/mole of antibody fragment.

The conjugates of the present invention, and the drug of Formula VIII, are useful in the method of inhibiting the growth of unwanted cells which is an important part of the present invention. Accordingly, the invention also includes pharmaceutical compositions, most preferably parenteral compositions suitable for injection into the body of the patient. Such compositions are formulated by methods which are commonly used in pharmaceutical chemistry. The present conjugates are acceptably soluble in physiologically-acceptable fluids, such as physiological saline solutions and other aqueous solutions which can safely be administered parenterally.

Products for parenteral administration are often formulated and distributed in solid, preferably freeze-dried form, for reconstitution immediately before use. Such formulations are useful compositions of the present invention. Their preparation is well understood by pharmaceutical chemists; in general, they comprise mixtures of inorganic salts, to confer isotonicity, and dispersing agents, such as lactose, to allow the dried preparation to dissolve quickly upon reconstitution. Such formulations are reconstituted with highly purified water to a known concentration, based on the drug.

The optimum dosage and administration schedule of conjugates of the present invention must be determined by the treating physician, in the light of the patient's condition.

It is customary, of course, to administer cytotoxic drugs in the form of divided doses, with intervals of days or weeks between each series of doses.

The specific purpose of the treatment, and the dose range to be administer, depends on the identity of the drug and the condition for which the patient is to be treated. Guidance as to the specific potencies of drugs and their appropriate dosage amounts and frequencies is to be obtained from the medical literature.

We claim:

1. A compound of the formula

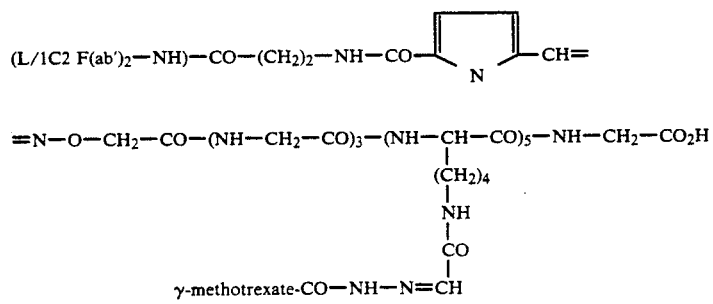

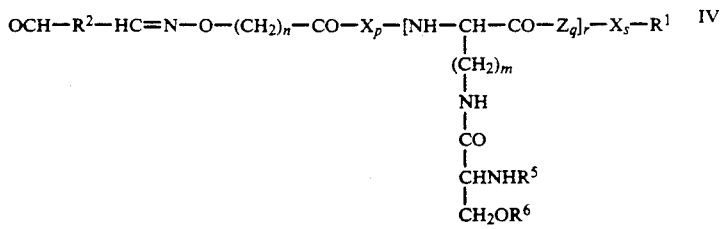

wherein
R[1] is a hydroxy group or a carboxy-protecting group;
X is —NH—(CH$_2$)$_t$—CO—;
Z is

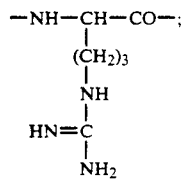 (A)

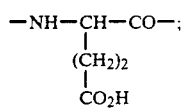 (B)

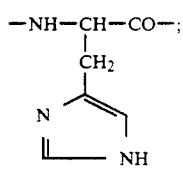 (C)

or

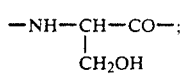 (D)

m is from 2 to about 6;
n is from 1 to about 4;
p is from 0 to about 5;
q is from 0 to about 3;
r is from 1 to about 10;
s is 0–2;
t is from 1 to about 3, and the values of t in the various X groups are independent of each other;
R[2] is C$_1$–C$_5$ alkylene, phenylene or pyrrolyl; R[5] is an amino-protecting group or hydrogen; R[6] is a hydroxy-protecting group or hydrogen.

2. A compound of claim 1 wherein t is 1; q is 0; r is from 3 to about 7; and p is from 0 to about 3.

3. A compound of claim 2 wherein R[2] is pyrrolyl; s is 1; and m is from about 4 to about 6.

4. A compound of the formula

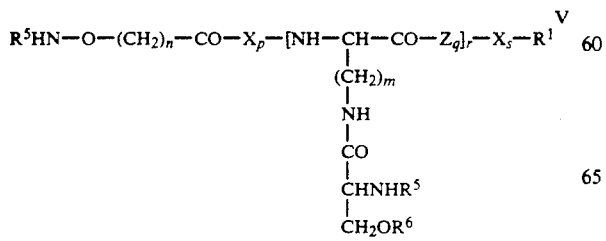 V wherein
R[1] is a hydroxy group or a carboxy-protecting group;
X is —NH—(CH$_2$)$_t$—CO—;
Z is

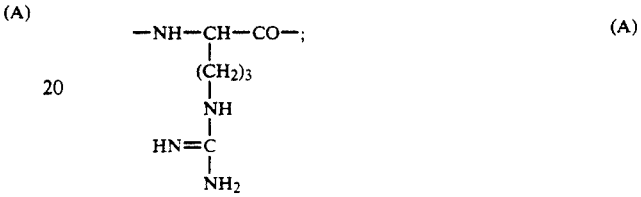 (A)

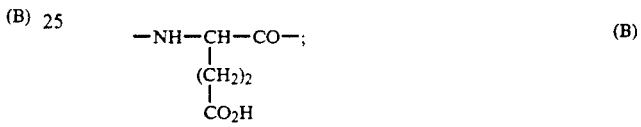 (B)

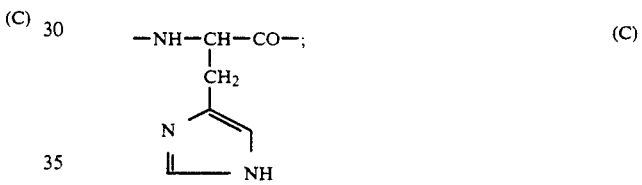 (C)

or

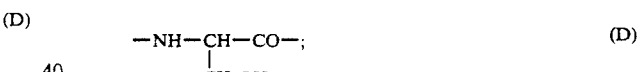 (D)

m is from 2 to about 6;
n is from 1 to about 4;
p is from 0 to about 5;
q is from 0 to about 3;
r is from 1 to about 10;
s is 0–2;
t is from 1 to about 3, and the values of t in the various X groups are independent of each other;
the R[5] groups represent the same or different amino-protecting groups or hydrogen; R[6] is a hydroxy-protecting group or hydrogen.

5. A compound of claim 4 wherein t is 1; q is 0; r is from 3 to about 7; and p is from 0 to about 3.

6. A compound of claim 5 wherein s is 1; and m is from about 4 to about 6.

7. A compound of the formula

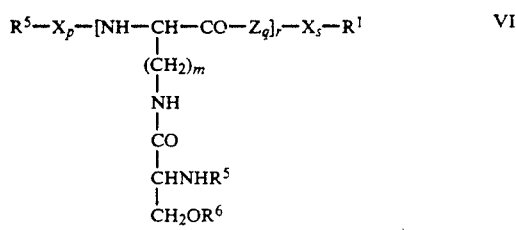 VI wherein $R^1$ is a hydroxy group or a carboxy-protecting group;

X is —NH—(CH$_2$)$_r$—CO—;

Z is

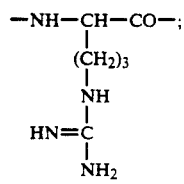 (A)

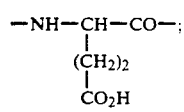 (B)

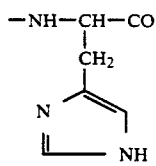 (C)

or

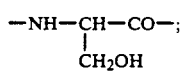 (D)

m is from 2 to about 6;
p is from 0 to about 5;
q is from 0 to about 3;
r is from 1 to about 10;
s is 0–2;
t is from 1 to about 3, and the values of t in the various X groups are independent of each other; the $R^5$ groups represent the same or different amino-protecting groups or hydrogen; $R^6$ is a hydroxy-protecting group or hydrogen.

8. A compound of claim 7 wherein t is 1; q is 0; r is from about 3 to about 7; and p is from 0 to about 3.

9. A compound of claim 8 wherein s is 1 and m is from about 4 to about 6.

* * * * *